US010265255B2

(12) United States Patent
Glenn, Jr. et al.

(10) Patent No.: US 10,265,255 B2
(45) Date of Patent: *Apr. 23, 2019

(54) METHOD OF TREATING HAIR

(71) Applicant: The Procter & Gamble Company, Cincinatti, OH (US)

(72) Inventors: Robert Wayne Glenn, Jr., Liberty Township, OH (US); Dariush Hosseinpour, Mason, OH (US); Kevin Lee Doyle, Fairfield, OH (US); Kathleen Mary Kaufman, Cincinatti, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/380,194

(22) Filed: Dec. 15, 2016

(65) Prior Publication Data

US 2017/0165162 A1 Jun. 15, 2017

Related U.S. Application Data

(60) Provisional application No. 62/267,566, filed on Dec. 15, 2015.

(51) Int. Cl.
| | |
|---|---|
| *A61Q 5/12* | (2006.01) |
| *A61K 8/46* | (2006.01) |
| *A61K 8/06* | (2006.01) |
| *A61K 8/33* | (2006.01) |
| *A61K 8/34* | (2006.01) |
| *A61K 8/41* | (2006.01) |
| *A61K 8/49* | (2006.01) |
| *A61K 8/92* | (2006.01) |
| *A61K 8/86* | (2006.01) |
| *A61K 8/04* | (2006.01) |

(52) U.S. Cl.
CPC ................ *A61K 8/46* (2013.01); *A61K 8/046* (2013.01); *A61K 8/06* (2013.01); *A61K 8/33* (2013.01); *A61K 8/34* (2013.01); *A61K 8/416* (2013.01); *A61K 8/49* (2013.01); *A61K 8/86* (2013.01); *A61K 8/922* (2013.01); *A61Q 5/12* (2013.01); *A61K 2800/21* (2013.01); *A61K 2800/34* (2013.01); *A61K 2800/413* (2013.01); *A61K 2800/87* (2013.01)

(58) Field of Classification Search
None
See application file for complete search history.

(56) References Cited

U.S. PATENT DOCUMENTS

| | | |
|---|---|---|
| 3,236,733 A | 2/1966 | Karsten et al. |
| 3,938,708 A | 2/1976 | Burger |
| 4,607,756 A | 8/1986 | Courtman |
| 4,610,874 A | 9/1986 | Matravers |
| 4,880,618 A | 11/1989 | Grollier et al. |
| 5,012,978 A | 5/1991 | Bolduc |
| 5,077,040 A | 12/1991 | Bergmann et al. |
| 5,635,469 A | 6/1997 | Fowler et al. |
| 5,674,478 A | 10/1997 | Dodd et al. |
| 5,985,295 A | 11/1999 | Peffly |
| 6,039,036 A | 3/2000 | Restle et al. |
| 6,589,509 B2 | 7/2003 | Keller et al. |
| 6,604,693 B2 | 8/2003 | Santagiuliana |
| 6,605,577 B1 | 8/2003 | Harrison et al. |
| 6,642,194 B2 | 11/2003 | Harrison et al. |
| 6,656,458 B1 | 12/2003 | Philippe et al. |
| 6,927,196 B2 | 8/2005 | Snyder et al. |
| 7,001,594 B1 | 2/2006 | Peffly et al. |
| 7,217,777 B2 | 5/2007 | Lange et al. |
| 7,316,815 B2 | 1/2008 | Philippe et al. |
| RE40,534 E | 10/2008 | Harrison et al. |
| 7,455,195 B2 | 11/2008 | Mekata |
| 7,462,585 B2 | 12/2008 | Uehara |
| 7,470,651 B2 | 12/2008 | Uehara et al. |
| 7,504,093 B2 | 3/2009 | Bracken et al. |
| 7,759,378 B2 | 7/2010 | Philippe et al. |
| 8,017,106 B2 | 9/2011 | Keller et al. |
| 8,263,053 B2 | 9/2012 | Duvel et al. |
| 8,475,777 B2 | 7/2013 | Rautschek |
| 8,476,472 B2 | 7/2013 | Hojo et al. |

(Continued)

FOREIGN PATENT DOCUMENTS

| | | |
|---|---|---|
| DE | 10304721 B4 | 3/2007 |
| EP | 978271 A1 | 2/2000 |

(Continued)

OTHER PUBLICATIONS

All Office Actions, U.S. Appl. No. 14/739,588.
All Office Actions, U.S. Appl. No. 14/739,670.
All Office Actions, U.S. Appl. No. 14/739,708.
All Office Actions, U.S. Appl. No. 14/739,755.
All Office Actions, U.S. Appl. No. 15/135,684.
All Office Actions, U.S. Appl. No. 15/135,691.
All Office Actions, U.S. Appl. No. 15/135,705.
All Office Actions, U.S. Appl. No. 15/135,715.
All Office Actions, U.S. Appl. No. 15/380,218.
All Office Actions, U.S. Appl. No. 15/380,261.

(Continued)

*Primary Examiner* — Jyothsna A Venkat
(74) *Attorney, Agent, or Firm* — Alexandra S. Anoff

(57) ABSTRACT

A method of treating the hair including providing a concentrated hair care composition in a mechanical foam dispenser. The concentrated hair care composition includes one or more oils, from about 1% to about 5% perfume, and has 0% high melting point fatty compounds. The method also includes dispensing the concentrated hair care composition from the mechanical foam dispenser as a dosage of foam; applying the foam to the hair; and rinsing the foam from the hair. The foam has a density of from about 0.025 g/cm³ to about 0.3 g/cm³ when dispensed from the mechanical foam dispenser.

9 Claims, No Drawings

(56) References Cited

U.S. PATENT DOCUMENTS

| | | |
|---|---|---|
| 8,642,021 B2 | 2/2014 | Brautigam et al. |
| 8,697,040 B2 | 4/2014 | Duvel et al. |
| 8,956,597 B2 | 2/2015 | Gesztesi et al. |
| 8,999,306 B2 | 4/2015 | Duvel et al. |
| 9,255,184 B2 | 2/2016 | Paul |
| 9,308,398 B2 | 4/2016 | Hutton et al. |
| 9,358,186 B2 | 6/2016 | Chandra et al. |
| 9,539,199 B2 | 1/2017 | Beer et al. |
| 9,539,208 B2 | 1/2017 | Tamarkin et al. |
| 9,540,489 B2 | 1/2017 | Panandiker et al. |
| 9,828,170 B2 | 11/2017 | Nomura et al. |
| 9,993,419 B2 | 6/2018 | Glenn, Jr. et al. |
| 2001/0008630 A1 | 7/2001 | Pyles et al. |
| 2001/0025857 A1 | 10/2001 | Baudin |
| 2002/0031532 A1 | 3/2002 | Uchiyama |
| 2002/0143063 A1 | 10/2002 | Alvarado |
| 2002/0197213 A1 | 12/2002 | Schmenger et al. |
| 2003/0152542 A1 | 8/2003 | Decoster et al. |
| 2003/0228272 A1 | 12/2003 | Amjad et al. |
| 2004/0018164 A1 | 1/2004 | Zofchak et al. |
| 2004/0076595 A1 | 4/2004 | Khan |
| 2004/0229763 A1 | 11/2004 | Hutton, III et al. |
| 2004/0247550 A1 | 12/2004 | Asari et al. |
| 2005/0002892 A1 | 1/2005 | Khan et al. |
| 2005/0136011 A1 | 6/2005 | Nekludoff et al. |
| 2005/0196372 A1 | 9/2005 | Cajan |
| 2005/0196376 A1 | 9/2005 | Loomis |
| 2005/0197421 A1 | 9/2005 | Loomis |
| 2005/0222001 A1 | 10/2005 | Baumeister et al. |
| 2005/0274737 A1 | 12/2005 | Krause et al. |
| 2006/0034792 A1 | 2/2006 | Lazzeri et al. |
| 2006/0054634 A1 | 3/2006 | Mekata |
| 2006/0083704 A1 | 4/2006 | Torgerson |
| 2006/0275245 A1 | 12/2006 | Decoster et al. |
| 2006/0292104 A1 | 12/2006 | Guskey et al. |
| 2006/0293197 A1 | 12/2006 | Uehara et al. |
| 2007/0179207 A1 | 8/2007 | Fernandez et al. |
| 2007/0286837 A1 | 12/2007 | Torgerson |
| 2008/0066773 A1 | 3/2008 | Anderson et al. |
| 2008/0138296 A1 | 6/2008 | Tamarkin et al. |
| 2008/0292560 A1 | 11/2008 | Tamarkin et al. |
| 2008/0292574 A1 | 11/2008 | Uehara |
| 2009/0041706 A1 | 2/2009 | Molenda et al. |
| 2009/0155383 A1 | 6/2009 | Kitko et al. |
| 2009/0232759 A1 | 9/2009 | Bell et al. |
| 2010/0092405 A1 | 4/2010 | Philippe et al. |
| 2010/0143280 A1 | 6/2010 | Yokogi et al. |
| 2010/0143281 A1 | 6/2010 | Okada et al. |
| 2010/0143282 A1 | 6/2010 | Yokogi et al. |
| 2010/0143425 A1 | 6/2010 | Okada et al. |
| 2010/0178265 A1 | 7/2010 | Molenda et al. |
| 2011/0135588 A1 | 6/2011 | Uehara et al. |
| 2011/0226273 A1 | 9/2011 | Deardorff et al. |
| 2011/0280110 A1 | 11/2011 | Chen |
| 2011/0318295 A1 | 12/2011 | Shimizu |
| 2012/0020908 A1 | 1/2012 | Paul |
| 2012/0034173 A1 | 2/2012 | Batt et al. |
| 2012/0043352 A1 | 2/2012 | Rasmussen et al. |
| 2012/0114819 A1 | 5/2012 | Ragnarsson |
| 2012/0171147 A1 | 7/2012 | Rautschek |
| 2012/0288465 A1 | 11/2012 | Loechel |
| 2013/0075430 A1 | 3/2013 | Ragnarsson |
| 2013/0202666 A1 | 8/2013 | Petkov et al. |
| 2013/0280192 A1 | 10/2013 | Carter et al. |
| 2013/0284196 A1 | 10/2013 | Murdock et al. |
| 2014/0105943 A1 | 4/2014 | Pistoria et al. |
| 2014/0107224 A1 | 4/2014 | Osman et al. |
| 2014/0116458 A1 | 5/2014 | Krueger |
| 2014/0135414 A1 | 5/2014 | Loomis |
| 2014/0237732 A1 | 8/2014 | Zuedel Fernandes et al. |
| 2014/0261517 A1 | 9/2014 | Humphreys et al. |
| 2014/0302103 A1 | 10/2014 | Carter et al. |
| 2014/0356303 A1 | 12/2014 | Rocco et al. |
| 2014/0377206 A1 | 12/2014 | Uehara et al. |
| 2015/0011450 A1 | 1/2015 | Carter et al. |
| 2015/0030643 A1 | 1/2015 | Gartstein et al. |
| 2015/0093420 A1 | 4/2015 | Snyder et al. |
| 2015/0190326 A1 | 7/2015 | Brouard et al. |
| 2015/0359725 A1 | 12/2015 | Glenn, Jr. et al. |
| 2015/0359726 A1 | 12/2015 | Glenn, Jr. et al. |
| 2015/0359727 A1 | 12/2015 | Glenn, Jr. et al. |
| 2015/0359728 A1 | 12/2015 | Glenn, Jr. et al. |
| 2016/0000673 A1 | 1/2016 | Ainger et al. |
| 2016/0310375 A1 | 4/2016 | Torres Rivera et al. |
| 2016/0310376 A1 | 4/2016 | Torres Rivera et al. |
| 2016/0143821 A1 | 5/2016 | Chang et al. |
| 2016/0309871 A1 | 10/2016 | Torres Rivera et al. |
| 2016/0310371 A1 | 10/2016 | Zhao et al. |
| 2016/0310372 A1 | 10/2016 | Glenn, Jr. et al. |
| 2016/0310377 A1 | 10/2016 | Torres Rivera et al. |
| 2016/0310397 A1 | 10/2016 | Johnson et al. |
| 2017/0087068 A1 | 3/2017 | Callens et al. |
| 2017/0165155 A1 | 6/2017 | Glenn, Jr. et al. |
| 2017/0165156 A1 | 6/2017 | Glenn, Jr. et al. |
| 2017/0165157 A1 | 6/2017 | Glenn, Jr. et al. |
| 2017/0165162 A1 | 6/2017 | Glenn, Jr. et al. |
| 2017/0165163 A1 | 6/2017 | Glenn, Jr. et al. |
| 2017/0165191 A1 | 6/2017 | Glenn, Jr. et al. |
| 2017/0174413 A1 | 6/2017 | Callens et al. |
| 2017/0304184 A1 | 10/2017 | Glenn, Jr. et al. |
| 2017/0304185 A1 | 10/2017 | Glenn, Jr. et al. |
| 2017/0304186 A1 | 10/2017 | Glenn, Jr. et al. |
| 2018/0168948 A1 | 6/2018 | Glenn, Jr. et al. |
| 2018/0168949 A1 | 6/2018 | Glenn, Jr. et al. |
| 2018/0168996 A1 | 6/2018 | Glenn, Jr. et al. |
| 2018/0221270 A1 | 8/2018 | Glenn, Jr. et al. |
| 2018/0256457 A1 | 9/2018 | Glenn, Jr. et al. |
| 2018/0256459 A1 | 9/2018 | Torres et al. |
| 2018/0256481 A1 | 9/2018 | Glenn, Jr. et al. |
| 2018/0353398 A1 | 12/2018 | Torres Rivera et al. |

FOREIGN PATENT DOCUMENTS

| | | |
|---|---|---|
| EP | 1002525 A2 | 5/2000 |
| EP | 1340485 A2 | 2/2003 |
| EP | 2138155 A2 | 12/2009 |
| EP | 2883533 A1 | 6/2015 |
| JP | H06227941 A | 8/1994 |
| JP | 2001302466 A | 10/2001 |
| JP | 3242689 B2 | 12/2001 |
| JP | 2003-119113 A | 4/2003 |
| JP | 2005232271 A | 9/2005 |
| JP | 2006182743 A | 7/2006 |
| JP | 2010-132569 A | 6/2010 |
| JP | 4694171 B2 | 6/2011 |
| JP | 2014-125477 A | 7/2014 |
| WO | WO 96/19188 A1 | 6/1996 |
| WO | WO 97/20626 A1 | 6/1997 |
| WO | WO 02/22085 * | 3/2002 |
| WO | WO0222085 A1 | 3/2002 |
| WO | WO 2004/078901 A1 | 9/2004 |
| WO | WO 2006/045170 * | 5/2006 |
| WO | WO 2013/176666 A1 | 11/2013 |

OTHER PUBLICATIONS

All Office Actions, U.S. Appl. No. 15/380,293.
All Office Actions, U.S. Appl. No. 15/380,345.
All Office Actions, U.S. Appl. No. 15/380,373.
All Office Actions, U.S. Appl. No. 15/135,712.
All Office Actions, U.S. Appl. No. 15/274,226.
All Office Actions, U.S. Appl. No. 15/381,298.
All Office Actions, U.S. Appl. No. 15/136,020.
All Office Actions, U.S. Appl. No. 15/136,032.
All Office Actions, U.S. Appl. No. 15/492,429.
All Office Actions, U.S. Appl. No. 15/492,451.
All Office Actions, U.S. Appl. No. 15/492,469.
Carolyn Evans: "Scalp Cleansing, Scalp Tonique, Hair Shampoo, Hair Conditioner, Demonstration" Youtube, Apr. 22, 2012, p. 2. First part of the video (0-3 min) dedicated to "scalp cleansing"; second part of the video (3-6 min) dedicated to the treatment of the hair.

(56) References Cited

OTHER PUBLICATIONS

Anonymous: "GNPD—Anti-Dandruff Shampoo", Nov. 1, 2012.
Anonymous "Shampoo only Scalp? or entire head?—The Long Hair Community Discussion Boards", Feb. 1, 2011, Retrieved from the internet: URL: http://forums.longhaircommunity.com/archieve/index.php/t-91788.html, retrieved on Jul. 21, 2016.
Samantha Zabell: "Mistakes You're Making Washing Your Hair—How You're Washing Your Hair Wrong", Jan. 14, 2014, Retrieved from the Internet: URL: http://www.goodhousekeeping.com/beauty/hair/tips/a19894/mistakes-washing-your-hair/, Section 3. "Overdoing it on shampoo and/or conditioner"; p. 2, retrieved on Jul. 21, 2016.
Anonymous: "GNPD—Anti-Dandruff Shampoo + Conditioner Set", Procter and Gamble China, Apr. 1, 2009, Mintel GNPD, Retrieved from the Internet: URL: http://www.gnpd.com/sinatra/recordpage/107827/from_search/EkXVQ1u6vF/?page=2, Retrieved on Jul. 12, 2016.
Database GNPD, Mintel; Aug. 2014 "Gold Olive Haircare Set".
Database GNPD Mintel; May 2014, "Coconut & Macadamia Oil Nourishing Shampoo and Nourishing Conditioner".
"Clarifying Shampoo", Mintel, Jun. 2015.
"Reinforcing conditioner", Mintel, May 2014.
Silsoft* 251, amine functional silicone microemulsion, Momentive Marketing Bulletin, 2012, 2 pages.
In-Cosmetics 2012: Wacker Introduced Novel Silicone Emulsions and New Hybrid Polymer for Hair-Care and Hair-Styling Products, Apr. 17, 2012, Munich.
PCT International Search Report and Written Opinion for PCT/US2016/066753 dated Feb. 28, 2017, 11 pages.
PCT International Search Report and Written Opinion for PCT/US2016/067916 dated Mar. 29, 2016.
PCT International Search Report and Written Opinion for PCT/US2016/028731 dated Jul. 5, 2016, 11 pages.
PCT International Search Report and Written Opinion for PCT/US2016/028860 dated Jul. 7, 2016, 11 pages.
PCT International Search Report and Written Opinion for PCT/US2015/035796 dated Sep. 14, 2015, 9 pages.
PCT International Search Report and Written Opinion for PCT/US2015/035756 dated Dec. 21, 2015, 13 pages.
PCT International Search Report and Written Opinion for PCT/US2015/035797 dated Sep. 14, 2015, 9 pages.
PCT International Search Report and Written Opinion for PCT/US2015/035799 dated Sep. 14, 2015, 9 pages.
PCT International Search Report and Written Opinion for PCT/US2016/028739 dated Jul. 4, 2016, 11 pages.
PCT International Search Report and Written Opinion for PCT/US2016/066755 dated Feb. 27, 2017, 12 pages.
PCT International Search Report and Written Opinion for PCT/US2016/066759 dated Feb. 27, 2017, 11 pages.
PCT International Search Report and Written Opinion for PCT/US2016/066754 dated Feb. 20, 2017, 11 pages.
PCT International Search Report and Written Opinion for PCT/US2016/028745 dated Aug. 8, 2016.
PCT International Search Report and Written Opinion for PCT/US2016/028853 dated Sep. 30, 2016, 19 pages.
PCT International Search Report and Written Opinion for PCT/US2016/028855, dated Oct. 5, 2016, 18 pages.
PCT International Search Report and Written Opinion for PCT/US2016/028743 dated Jul. 25, 2016.
All final and non-final office actions for U.S. Appl. No. 15/843,069.
All final and non-final office actions for U.S. Appl. No. 15/843,146.
All final and non-final office actions for U.S. Appl. No. 15/843,178.
All final and non-final office actions for U.S. Appl. No. 15/946,275.
All final and non-final office actions for U.S. Appl. No. 15/972,763.
All final and non-final office actions for U.S. Appl. No. 15/973,845.
All final and non-final office actions for U.S. Appl. No. 15/978,667.
All final and non-final office actions for U.S. Appl. No. 16/104,343.
All final and non-final Office Actions, U.S. Appl. No. 15/135,715.
Fabida. https://makeupandbeauty.com/head-shoulders-anti-dandruff-itchy-scalp-care-shampoo-review/. Published Jun. 26, 2012.
Free Sample. https://web.archive.org/web/20111116042029/http://freesampleprincess.com/head-and-shoulders-itchy-scalp-care-free-sample. Published Nov. 16, 2011.
Hair Conditioner Tips and Tricks. https://web.archive.org/web/20121106125731/http://www.thehairstyler.com/features/ articles/hair-care/hair-conditioner-tips-and-tricks. Published Nov. 6, 2012.
Mommy Story, http://www.amommystory.com/2011/11/head-shoulders-eucalyptus-itchy-scalp-care-to-the-rescue-review-giveaway.html. Published Nov. 21, 2011.
PCT International Search Report and Written Opinion for PCT/US2017/028472 dated Jun. 29, 2017.
PCT International Search Report and Written Opinion for PCT/US2017/028473 dated Jun. 29, 2017.
PCT International Search Report and Written Opinion for PCT/US2017/028474 dated Jun. 29, 2017.
PCT International Search Report and Written Opinion for PCT/US2017/066561 dated Apr. 4, 2018.
PCT International Search Report and Written Opinion for PCT/US2017/066563 dated Apr. 4, 2018.
Stylecaster. http://stylecaster.com/beauty/how-to-get-rid-of-dandruff/. Published: Jan. 16, 2014.
Xiameter Mem-0949 Emulsion (Nov. 2011).
U.S. Appl. No. 15/843,069, filed Dec. 15, 2017, Glenn, Jr. et al.
U.S. Appl. No. 15/843,146, filed Dec. 15, 2017, Glenn, Jr. et al.
U.S. Appl. No. 15/843,178, filed Dec. 15, 2017, Glenn, Jr. et al.
U.S. Appl. No. 16/104,343, filed Aug. 17, 2018, Torres Rivera et al.
U.S. Appl. No. 15/978,667, filed May 14, 2018, Glenn, Jr. et al.
U.S. Appl. No. 15/972,763, filed May 7, 2018, Torres Rivera et al.
U.S. Appl. No. 15/946,275, filed Apr. 5, 2018, Glenn, Jr. et al.
U.S. Appl. No. 15/973,845, filed May 8, 2018, Glenn, Jr. et al.

* cited by examiner

METHOD OF TREATING HAIR

FIELD OF THE INVENTION

Described herein is a method of treating hair with a concentrated hair conditioning composition comprising one or more oils provided in a mechanical foam dispenser.

BACKGROUND OF THE INVENTION

Today's hair conditioners almost universally comprise high levels of high melting point fatty compounds, the most common of which are C16 to C18 fatty alcohols. These high melting point fatty compounds are employed as structuring agents wherein they are combined with one or more surfactants and an aqueous carrier to form a gel network. The gel network increases the viscosity and yield point which facilitates the dispensing of the conditioner from a bottle or tube and the subsequent distribution and spreading of the product through the hair by the consumer. The gel network structuring also enables incorporation of silicones, perfumes and oils in the form of an oil-in-water emulsion that is phase stable. The silicones and oils are intended to be deposited on the hair to provide the primary hair conditioning benefits including wet and dry combing friction reduction and improved hair manageability.

However, today's gel network hair conditioners can lead to excessive co-deposits of the high melting point fatty compound on the hair over multiple cycles. These co-deposits can lead to significant waxy build-up on hair and weight the hair down. Indeed, one of the major consumer complaints with hair conditioners is often waxy residue which can make hair look greasy or feel heavy. Many current gel network hair conditioners deposit up to 10 times more high melting point fatty compounds (fatty alcohols) than silicones or oils after approximately 10 treatment cycles in technical testing. While not being bound to theory, this is hypothesized to be due to the approximately up to 10× greater concentration of high melting point fatty compounds in the product relative to the silicone or oil. However, such a high level of melting point fatty compounds (fatty alcohols) has been required to produce a shelf stable gel network with sufficient structuring for consumer acceptable viscosity and rheology.

There is also a desire by many consumers for conditioners that are free from ingredients that are perceived as being non-natural or "synthetic" including non-silicone containing products. These non-silicone conditioners may incorporate oils that are derived from natural sources including vegetable based oils and oil derivatives.

Described herein is a non-silicone concentrated hair care conditioner composition that enables new product opportunities and consumer benefits by addressing the previously described disadvantages associated with conventional gel network conditioners and which incorporates oils in the form of a nano-emulsion. Is has been found that concentrated, ultra-low viscosity hair conditioner compositions can be delivered to the hair in foamed form. These new concentrated oil nanoemulsion compositions enable sufficient dosage from a low density foam delivery form while also substantially eliminating the need for high melting point fatty compounds or other "insoluble" structurants (from "wax" structured to "gas" structured) that can lead to significant co-deposits, build-up and weigh down of hair. The net result has been a step change improvement in oil deposition purity versus today's rinse-off conditioners and an improvement in technical performance benefits from such a pure and transparent deposited oil layer. These benefits can include multicycle hair conditioning without hair weigh down, durable conditioning, reduced hair dye fade, and increased color vibrancy.

Nanoemulsion technology development is hindered by complex stability issues that emerge when droplet sizes are driven to the nanoscale. This is especially problematic in the presence of higher levels of perfume oils required for such a concentrated product. The concentrated hair care composition described herein is therefor also focused on improved stability.

SUMMARY OF THE INVENTION

Described herein is a method of treating the hair, the method comprising (1) providing a concentrated hair care composition in a mechanical foam dispenser, wherein the concentrated hair care composition comprises (a) from about 3% to about 25% of one or more oils, by weight of the concentrated hair care composition, wherein the particle size of the one or more oils is from about 1 nm to about 100 nm; and (b) from about 1% to about 5% perfume, by weight of the concentrated hair care composition; wherein the concentrated hair care composition comprises about 0% high melting point fatty compounds; wherein the concentrated hair care composition has a liquid phase viscosity of from about 1 centipoise to about 80 centipoise; wherein the concentrated hair care composition has a oil to high melting point fatty compound ratio of about 100:0 by weight of the oil and by weight of the high melting point fatty compound; and wherein the concentrated hair care composition has a oil to perfume ratio of from about 95:5 to about 50:50 by weight of the oil and by weight of the perfume; (2) dispensing the concentrated hair care composition from the mechanical foam dispenser as a dosage of foam; (3) applying the foam to the hair; and (4) rinsing the foam from the hair; wherein the foam has a density of from about 0.05 g/cm$^3$ to about 0.20 g/cm$^3$ when dispensed from the mechanical foam dispenser.

Also described herein is a mechanical foam dispenser comprising a concentrated hair care composition, the concentrated hair care composition comprising (1) from about 3% to about 25% of one or more oils, by weight of the concentrated hair care composition, wherein the particle size of the one or more oils is from about 1 nm to about 100 nm; and (2) from about 1% to about 5% perfume, by weight of the concentrated hair care composition, by weight of the concentrated hair care composition; wherein the concentrated hair care composition comprises about 0% high melting point fatty compounds; wherein the concentrated hair care composition has a liquid phase viscosity of from about 1 centipoise to about 80 centipoise; wherein the concentrated hair care composition has a oil to high melting point fatty compound ratio of about 100:0 by weight of the oil and by weight of the high melting point fatty compound; wherein the concentrated hair care composition has a oil to perfume ratio of from about 95:5 to about 50:50 by weight of the oil and by weight of the perfume; wherein the foam has a density of from about 0.05 g/cm$^3$ to about 0.2 g/cm$^3$ when dispensed from the mechanical foam dispenser; and wherein the concentrated hair care composition is rinse-off.

DETAILED DESCRIPTION OF THE INVENTION

While the specification concludes with claims particularly pointing out and distinctly claiming the invention, it is believed that the concentrated hair care composition described herein will be better understood from the following description.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated.

As used herein, the terms "include," "includes," and "including," are meant to be non-limiting and are understood to mean "comprise," "comprises," and "comprising," respectively.

As used herein, the term "concentrated" means a hair care composition comprising from about 3% to about 25% of one or more oils, by weight of the hair care composition.

As used herein, the term "nanoemulsion" means an oil-in-water (o/w) emulsion with an average particle size ranging from about 1 nm to about 100 nm. The particle size referred to herein is z-average measured by dynamic light scattering. The nanoemulsion described herein may be prepared by the following methods: (1) mechanically breaking down the emulsion droplet size; (2) spontaneously forming the emulsion (may be referred to as a microemulsion in the literature); and (3) using emulsion polymerization to achieve average particle size in the target range described herein.

The method of preparing the nanoemulsion can be a mechanical method in which the nanoemulsion is prepared via the following steps: (1) a primary surfactant is dissolved in water, (2) a oil is added, and a two-phase mixture is formed, (3) with simple mixing, a co-surfactant is slowly added to the two-phase mixture, until a clear isotropic microemulsion of a siloxane-in-water is formed.

The second method of preparing the nanoemulsion may be by emulsion polymerization. Emulsion polymerization methods for making nanoemulsions of polymers involve starting with polymer precursors, i.e., monomers, or reactive oligomers, which are immiscible in water; a surfactant to stabilize polymer precursor droplets in water; and a water soluble polymerization catalyst. Typically, the catalyst is a strong mineral acid such as hydrochloric acid, or a strong alkaline catalyst such as sodium hydroxide. These components are added to water, the mixture is stirred, and polymerization is allowed to advance until the reaction is complete, or the desired degree of polymerization (DP) is reached, and an emulsion of the polymer is formed.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Hair Care Composition

The method of treating the hair described herein comprises providing a concentrated hair care composition in a mechanical foam dispenser. The concentrated hair care composition comprises one or more oils.

A. Oil Deposition Purity

The method of treating hair comprises dispensing the concentrated hair care composition described herein from the mechanical foam dispenser as a dosage of foam. The foam may comprise a oil deposition purity of from about 90% to about 100% after applying the foam to the hair and rinsing the foam from the hair.

Deposition Purity can be determined by the ratio of oil deposited per weight of hair to the total deposition of other ingredients per weight of hair. The amount of oil is determined by either extraction or digestion of the hair followed by an analysis with a quantitative technique such as gas chromatography. The total deposition may be determined by the sum of separate deposition measurements or by a Single Inclusive Measurement of total deposition. The separate deposition measurements may include but are not limited to fatty alcohols, EGDS, quaternized agents, and oil. Typically these measurements involve extracting the hair then separating the ingredients of interest with chromatography and quantifying with an externally calibration based on test solution concentration. The Single Inclusive Measurement of total deposition is gravimetric. The hair is thoroughly extracted and the residue determined by weighing the dissolved residue in the extract after evaporating the solvent. This residue contains both deposited ingredients and naturally occurring extractable compounds from the hair (primarily lipids). The naturally occurring extractable compounds are quantified and subtracted from the total. These include: fatty acids, squalene, cholesterol, ceramides, wax esters, triglycerides and sterol esters. The method of quantitation is similar to the deposition measurements. Other supporting evidence of Deposition Purity may include spectroscopic or topography mapping of the hair surface.

B. Oils

The concentrated hair care composition may comprise from about 3% to about 25%, alternatively from about 4% to about 20%, alternatively from about 5% to about 15% of one or more oils, and alternatively from about 8% to about 15% of one or more oils by weight of the concentrated hair care composition. The particle size of the one or more oils may be from about 1 nm to about 100 nm, alternatively from about 5 nm to about 80 nm, alternatively from about 10 nm to about 60 nm, and alternatively from about 12 nm to about 50 nm. The oils described herein are silicone-free.

The particle size of the one or more oils can be measured by dynamic light scattering (DLS) using a 173° measurement angle and the refractive index of the one or more oils. A Malvern Zetasizer Nano ZEN3600 system (www.malvern.com) using He—Ne laser 633 nm can be used for the measurement at 25° C.

Zetasizer Software provided by Malvern Instruments can be used for data analysis. For each sample, 3 measurements should be made and Z-average values should be reported as the particle size.

In an embodiment, the one or more oils may be in the form of a nanoemulsion. The nanoemulsion may comprise any oil suitable for application to the skin and/or hair. In an embodiment, the one or more oils include low melting point non-silicone oils having a melting point of from about −50 degrees Celsius to about 38 degrees Celsius, alternatively from about −45 degrees Celsius to about 35 degrees Celsius, alternatively from about −40 degrees Celsius to about 30 degrees Celsius, alternatively from about −35 degrees Celsius to about 25 degrees Celsius, and alternatively from about −25 degrees Celsius to about 25 degrees Celsius. The low melting point oil useful herein can be chosen from vegetable oils, sucrose polyesters, alkenyl esters, hydrocarbon oils, pentaerythritol ester oils, trimethylol ester oils, citrate ester oils, glyceryl ester oils, poly alpha-olefin oils, metathesized oligomer oils, polyoils, and mixtures thereof.

The one or more oils may comprise:

Vegetable Oils

The one or more oils may comprise one or more vegetable oils which can be liquid at room temperature. In an embodiment, acceptable vegetable oils are those with a melting point not exceeding 85 degrees Celsius. Exemplary vegetable oils can include palm oil, soybean oil, rapeseed oil, sunflower oil, peanut oil, cottonseed oil, palm kernel oil, coconut oil, olive oil, algae extract, borage seed oil, carrageenan extract, castor oil, corn oil, evening primrose oil, grape seed oil, jojoba oil, kukui nut oil, lecithin, macadamia oil, oat kernel meal oil, pea extract oil, pecan oil, safflower oil, sesame oil, shea butter, soybean oil, sunflower oil, hazelnut oil, linseed oil, rice bran oil, canola oil, flaxseed oil, walnut oil, almond oil, cocoa butter, and/or sweet almond oil.

Sucrose Polyesters

The one or more oils may comprise one or more sucrose polyesters. Sucrose polyesters are polyester materials having multiple substitution positions around the sucrose backbone coupled with the chain length, saturation, and derivation variables of the fatty chains. Such sucrose polyesters can have an esterification ("IBAR") of greater than about 5. In an embodiment, the one or more sucrose polyesters may have an IBAR of from about 5 to about 8, alternatively from about 5 to about 7, alternatively about 6, and alternatively about 8. As sucrose polyesters are derived from a natural resource, a distribution in the IBAR and chain length may exist. For example a sucrose polyester having an IBAR of 6, may contain a mixture of mostly IBAR of about 6, with some IBAR of about 5 and some IBAR of about 7. Additionally, such sucrose polyesters may have a saturation or iodine value ("IV") from about 3 to about 140, alternatively from about 10 to about 120, alternatively from about 20 to about 100. Further, such sucrose polyesters can have a chain length from about C12 to about C20. Non-limiting examples of sucrose polyesters suitable for use include SEFOSE® 1618S, SEFOSE® 1618U, SEFOSE® 1618H, Sefa Soyate IMF 40, Sefa Soyate LP426, SEFOSE® 2275, SEFOSE® C1695, SEFOSE® C18:0 95, SEFOSE® C1495, SEFOSE® 1618H B6, SEFOSE® 1618S B6, SEFOSE® 1618U B6, Sefa Cottonate, SEFOSE® C1295, Sefa C895, Sefa C1095, SEFOSE® 1618S B4.5, all available from The Procter and Gamble Co. of Cincinnati, Ohio.

Alkenyl Esters:

The one or more oils may include one or more alkenyl esters. Non-limiting examples of alkenyl esters can include oleyl myristate, oleyl stearate, oleyl oleate, and combinations thereof.

Hydrocarbon Oils:

The one or more oils may include one or more hydrocarbon oils. Non-limiting examples of hydrocarbon oils include differing grades and molecular weights of mineral oil, liquid isoparaffin, polyisobutene, and petrolatum.

Pentaerythritol Ester Oils and Trimethylol Ester Oils:

The one or more oils may include one or more pentaerythritol ester oils and/or one or more trimethylol ester oils. Non-limiting examples of pentaerythritol ester oils and trimethylol ester oils can include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and from Shin-nihon Rika with tradenames PTO and ENUJERUBU TP3SO.

Citrate Ester Oils:

The one or more oils may include one or more citrate ester oils. Non-limiting examples of citrate ester oils can include triisocetyl citrate with tradename CITMOL 316 available from Bernel, triisostearyl citrate with tradename PELEMOL TISC available from Phoenix, and trioctyldodecyl citrate with tradename CITMOL 320 available from Bernel.

Glyceryl Ester Oils:

The one or more oils may include one or more glyceryl ester oils. Non-limiting examples of glyceryl ester oils can include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Poly Alpha-Olefin Oils:

The one or more oils may include one or more poly alpha-olefin oils. Non-limiting examples of poly α-olefin oils can include polydecenes with tradenames PURESYN 6 having a number average molecular weight of about 500, PURESYN 100 having a number average molecular weight of about 3000, and PURESYN 300 having a number average molecular weight of about 6000, all available from Exxon Mobil Co.

Metathesized Oligomer Oils:

The one or more oils may include one or more metathesized oligomer oils derived from metathesis of unsaturated polyol esters in amounts by weight of the composition ranging from about 0.01% to about 5%, alternatively from about 0.1% to about 1%, and alternatively from about 0.25% to about 5%. Exemplary metathesized unsaturated polyol esters and their starting materials are set forth in U.S. Patent Application U.S. 2009/0220443 A1, which is incorporated herein by reference.

A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis). Self-metathesis may be represented schematically as shown in Equation 1:

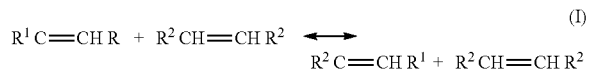

where $R^1$ and $R^2$ are organic groups.

Cross-metathesis may be represented schematically as shown Equation II:

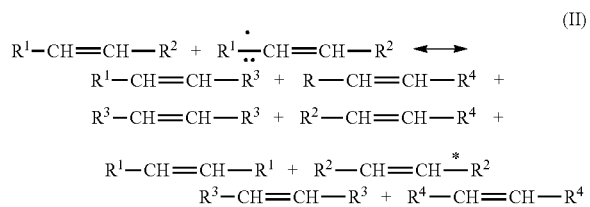

where $R^1$, $R^2$, $R^3$, and $R^4$ are organic groups.

When the unsaturated poyol ester comprises moleculest have more than one carbon-carbon double bond (i.e., a polyunsaturated polyol ester), self-metathesis results in oligomerization of the unsaturated polyol ester. The self-metathesis reaction results in the formation of metathesis dimers, metathesis trimers, and metathesis tetramers. Higher order metathesis oligomers, such as metathesis pentamers and metathesis hexamers, may also be formed by continued self-metathesis and will depend on the number and type of chains connecting the unsaturated polyol ester material as well as the number of esters and orientation of the ester relative to the unsaturation.

As a starting material, metathesized unsaturated polyol esters are prepared from one or more unsaturated polyol esters. As used herein, the term "unsaturated polyol ester" refers to a compound having two or more hydroxyl groups wherein at least one of the hydroxyl groups is in the form of an ester and wherein the ester has an organic group including at least one carbon-carbon double bond. In many embodiments, the unsaturated polyol ester can be represented by the general structure I:

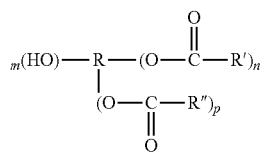

where n>1; m>0; p>0; (n+m+p)>2; R is an organic group; R is an organic group having at least one carbon-carbon double bond; and R is a saturated organic group. Exemplary embodiments of the unsaturated polyol ester are described in detail in U.S. 2009/0220443 A1.

In an embodiment, the unsaturated polyol ester is an unsaturated ester of glycerol. Sources of unsaturated polyol esters of glycerol include synthesized oils, natural oils (e.g., vegetable oils, algae oils, bacterial derived oils, and animal fats), combinations of these, and the like. Recycled used vegetable oils may also be used. Representative examples of vegetable oils include argan oil, canola oil, rapeseed oil, coconut oil, corn oil, cottonseed oil, olive oil, palm oil, peanut oil, safflower oil, sesame oil, soy-bean oil, sunflower oil, high oleoyl soy-bean oil, high oleoyl sunflower oil, linseed oil, palm kernel oil, tung oil, castor oil, high oloeyl sunflower oil, high oleoyl soybean oil, high erucic rape oils, Jatropha oil, combinations of theses, and the like. Representative examples of animal fats include lard, tallow, chicken fat, yellow grease, fish oil, combinations of these, and the like. A representative example of a synthesized oil includes tall oil, which is a byproduct of wood pulp manufacture.

Other examples of unsaturated polyol esters can include diesters such as those derived from ethylene glycol or propylene glycol, esters such as those derived from pentaerythritol or dipentaerythritol, or sugar esters such as SEFOSE®. Sugar esters such as SEFOSE® include one or more types of sucrose polyesters as described herein, with up to eight ester groups that could undergo a metathesis exchange reaction. Other examples of suitable natural polyol esters may include but not be limited to sorbitol esters, maltitol esters, sorbitan esters, maltodextrin derived esters, xylitol esters, and other sugar derived esters.

In an embodiment, chain lengths of esters are not restricted to C8-C22 or even chain lengths only and can include natural esters that come from co-metathesis of fats and oils with short chain olefins both natural and synthetic providing a polyol ester feedstock which can have even and odd chains as well as shorter and longer chains for the self metathesis reaction. Suitable short chain olefins include ethylene and butene.

The oligomers derived from the metathesis of unsaturated polyol esters may be further modified via hydrogenation. For example, in an embodiment, the oligomer can be about 60% hydrogenated or more; in certain embodiments, about 70% hydrogenated or more; in certain embodiments, about 80% hydrogenated or more; in certain embodiments, about 85% hydrogenated or more; in certain embodiments, about 90% hydrogenated or more; and in certain embodiments, generally 100% hydrogenated.

In some embodiments, the triglyceride oligomer is derived from the self-metathesis of soybean oil. The soy oligomer can include hydrogenated soy polyglycerides. The soy oligomer may also include C15-C23 alkanes, as a byproduct. An example of metathesis derived soy oligomers is the fully hydrogenated DOW CORNING® HY-3050 soy wax, available from Dow Corning.

In other embodiments, the metathesized unsaturated polyol esters can be used as a blend with one or more non-metathesized unsaturated polyol esters. The non-metathesized unsaturated polyol esters can be fully or partially hydrogenated. Such an example is DOW CORNING® HY-3051, a blend of HY-3050 oligomer and hydrogenated soybean oil (HSBO), available from Dow Corning. In some embodiments of the invention, the non-metathesized unsaturated polyol ester is an unsaturated ester of glycerol. Sources of unsaturated polyol esters of glycerol include synthesized oils, natural oils (e.g., vegetable oils, algae oils, bacterial derived oils, and animal fats), combinations of theses, and the like. Recycled used vegetable oils may also be used. Representative examples of vegetable oils include those listed above.

Other modifications of the polyol ester oligomers can be partial amidation of some fraction of the esters with ammonia or higher organic amines such as dodecyl amine or other fatty amines. This modification will alter the overall oligomer composition but can be useful in some applications providing increased lubricity of the product. Another modification can be via partial amidation of a poly amine providing potential for some pseudo cationic nature to the polyol ester oligomers. Such an example is DOW CORN- ING® material HY-3200, Other exemplary embodiments of amido functionalized oligomers are described in detail in WO2012006324A1, which is incorporated herein by reference.

The polyol ester oligomers may be modified further by partial hydroformylation of the unsaturated functionality to provide one or more OH groups and an increase in the oligomer hydrophilicity.

In an embodiment, the unsaturated polyol esters and blends can be modified prior to oligomerization to incorporate near terminal branching, Exemplary polyol esters modified prior to oligomerization to incorporate terminal branching are set forth in WO2012/009525 A2, which is incorporated herein by reference.

C. Nonionic Emulsifiers

The concentrated hair care composition may comprise from about 3% to about 20%, alternatively from about 5% to about 15%, and alternatively from about 7.5% to about 12% of a nonionic emulsifier, by weight of the concentrated hair care composition. Nonionic emulsifiers may be broadly defined as including compounds containing an alkylene oxide groups (hydrophilic in nature) with a hydrophobic compound, which may be aliphatic or alkyl aromatic in nature. Examples of nonionic emulsifiers include:

1. Alcohol ethoxylates which are condensation products of aliphatic alcohols having from about 8 to about 18 carbon atoms, in either straight chain or branched chain configuration, with from about 2 to about 35 moles of ethylene oxide, e.g., a coconut alcohol ethylene oxide condensate having from about 2 to about 30 moles of ethylene oxide per mole of coconut alcohol, the coconut alcohol fraction having from about 10 to about 14 carbon atom.

2. The polyethylene oxide condensates of alkyl phenols, e.g., the condensation products of the alkyl phenols having an alkyl group containing from about 6 to about 20 carbon atoms in either a straight chain or branched chain configuration, with ethylene oxide, the said ethylene oxide being present in amounts equal to from about 3 to about 60 moles of ethylene oxide per mole of alkyl phenol.

3. Those derived from the condensation of ethylene oxide with the product resulting from the reaction of propylene oxide and ethylene di amine products.

4. Long chain tertiary amine oxides such as those corresponding to the following general formula: R1 R2 R3 N-->O wherein R1 contains an alkyl, alkenyl or monohydroxy alkyl radical of from about 8 to about 18 carbon atoms, from 0 to about 10 ethylene oxide moieties, and from 0 to about 1 glyceryl moiety, and R2 and R3 contain from about 1 to about 3 carbon atoms and from 0 to about 1 hydroxy group, e.g., methyl, ethyl, propyl, hydroxyethyl, or hydroxypropyl radicals (the arrow in the formula represents a semipolar bond).

5. Long chain tertiary phosphine oxides corresponding to the following general formula: RR'R"P-->O wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula represents a semipolar bond.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.

7. Polysorbates, e.g., sucrose esters of fatty acids. Such materials are described in U.S. Pat. No. 3,480,616, e.g., sucrose cocoate (a mixture of sucrose esters of a coconut acid, consisting primarily of monoesters, and sold under the tradenames GRILLOTEN LSE 87K from RITA, and CRODESTA SL-40 from Croda).

8. Alkyl polysaccharide nonionic emulsifiers are disclosed in U.S. Pat. No. 4,565,647, Henado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group. The polysaccharide can contain from about 1.0 to about 10, alternatively from about 1.3 to about 3, and alternatively from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units. Optionally there can be a polyalkyleneoxide chain joining the hydrophobic moiety and the polysaccharide moiety. The alkyl group preferably contains up to about 3 hydroxy groups and/or the polyalkyleneoxide chain can contain up to about 10, preferably less than 5, alkylene moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses.

9. Polyethylene glycol (PEG) glyceryl fatty esters, as depicted by the formula RC(O)OCH2 CH(OH)CH2 (OCH2 CH2)n OH wherein n is from about 5 to about 200, preferably from about 20 to about 100, more preferably from about 30 to about 85, and RC(O)— is an ester wherein R comprises an aliphatic radical having from about 7 to 19 carbon atoms, preferably from about 9 to 17 carbon atoms, more preferably from about 11 to about 17 carbon atoms, most preferably from about 11 to 14 carbon atoms. In an embodiment, the combinations of n may be from about 20 to about 100, with C12-C18, alternatively C12-C15 fatty esters, for minimized adverse effect on foaming.

In an embodiment, the nonionic emulsifier may have a hydrocarbon chain length of from about 16 to about 20 carbon atoms and from about 20 to about 25 moles of ethoxylate.

In an embodiment, the nonionic emulsifier may have a hydrocarbon chain length of from about 19 to about 11, alternatively from about 9 to about 11 carbon atoms, and from about 2 to about 4 moles of ethoxylate.

In an embodiment, the nonionic emulsifier may comprise a combination of (a) a nonionic emulsifier of secondary alcohol having a hydrocarbon chain that has a length from about 11 to about 15 carbon atoms, and has from about 5 to about 9 moles of ethoxylate; and (b) a nonionic emulsifier having a hydrocarbon chain that has a length of from about 11 to about 13 carbon atoms and has from about 9 to about 12 moles of ethoxylate.

The nanoemulsion may be prepared using a mechanical method via the following steps: (1) a primary surfactant is dissolved in water, (2) a oil is added, and a two-phase mixture is formed, (3) with simple mixing, a co-surfactant is slowly added to the two-phase mixture, until a clear isotropic microemulsion of a siloxane-in-water is formed.

In an embodiment, the nonionic emulsifier in the formulation has hydrocarbon chain length of 16-20 and 20-25 ethoxylate mole.

In an embodiment, the hydrocarbon chain length and the ethoxylate mole number for the nonionic emulsifer is 9-11 and 2-4, respectively.

In an embodiment the nonionic emulsifier system consists of a) C11-15 with 5-9 ethoxylate moles in branched configuration b) linear nonionic emulsifier with C11-13 hydrocarbon chain length and 9-12 moles of ethoxylate.

D. Perfume

The concentrated hair care composition may comprise from about 1% to about 5%, alternatively from about 1.5% to about 4.5%, and alternatively from about 2% to about 4% perfume, by weight of the concentrated hair care composition.

In an embodiment, the concentrated hair care composition may have a oil to perfume ratio of from about 95:5 to about 50:50, alternatively from about 90:10 to about 60:40, and alternatively from about 85:15 to about 70:30, by weight of the oil and by weight of the perfume.

Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the concentrated hair care composition.

E. High Melting Point Fatty Compounds

The concentrated hair care composition may be substantially free of high melting point fatty compounds, alternatively less than about 1%, alternatively less than about 0.5%, alternatively less than about 0.25%, alternatively less than 0.1%, alternatively from about 0.01% to about 1%, alternatively 0% high melting point fatty compounds, by weight of the concentrated hair care composition. The concentrated hair care composition may have a oil to high melting point fatty compounds ratio of about 100:0 by weight of the oil and by weight of the high melting point fatty compounds.

The high melting point fatty compounds have a melting point of about 25° C. or higher, and are selected from the group consisting of fatty alcohols, fatty acids, fatty alcohol derivatives, fatty acid derivatives, and mixtures thereof. It is understood by the artisan that the high melting point fatty compounds disclosed in this section can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section.

Nonlimiting examples of the high melting point compounds are found in *International Cosmetic Ingredient Dictionary*, Fifth Edition, 1993, and *CTFA Cosmetic Ingredient Handbook*, Second Edition, 1992.

The fatty alcohols described herein are those having from about 14 to about 30 carbon atoms, alternatively from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids useful herein are those having from about 10 to about 30 carbon atoms, alternatively from about 12 to about 22 carbon atoms, and alternatively preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; C16-C30 alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

In an embodiment, the fatty compound may be a single high melting point compound of high purity. Single compounds of pure fatty alcohols selected may be selected from the group consisting of pure cetyl alcohol, stearyl alcohol, and behenyl alcohol. By "pure" herein, what is meant is that the compound has a purity of at least about 90%, alternatively at least about 95%.

Commercially available high melting point fatty compounds described herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago, Ill. USA), HYSTRENE available from Witco Corp. (Dublin, Ohio USA), and DERMA available from Vevy (Genova, Italy).

F. Cationic Surfactants

In an embodiment, the concentrated hair care composition may comprise about 0%, alternatively from about 0.25% to about 5%, alternatively from about 0.5% to about 4%, and alternatively from about 1% to about 3% cationic surfactants, by weight of the concentrated hair care composition.

The cationic surfactant may be a mono-long alkyl quaternized ammonium salt having the formula (XIII) [from WO2013148778]:

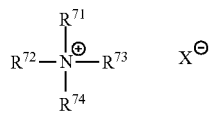

(XIII)
wherein one of $R^{71}$, $R^{72}$ $R^{73}$ and $R^{74}$ selected from an aliphatic group of from about 14 to about 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$ $R^{73}$ and $R^{74}$ are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and X is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$ $R^{73}$ and $R^{74}$ is selected from an alkyl group of from about 14 to about 30 carbon atoms, more preferably from about 16 to about 22 carbon atoms, still more preferably from about 16 to about 18 carbon atoms; the remainder of $R^{71}$, $R^{72}$, $R^{73}$, and $R^{74}$ are independently selected from the group consisting of $CH_3$, $C_2H_5$, $C_2H_4OH$, $CH_2C_5H_5$, and mixtures thereof; and (X) is selected from the group consisting of Cl, Br, $CH_3OSO_3$, and mixtures thereof. It is believed that such mono-long alkyl quaternized ammonium salts can provide improved slippery and slick feel on wet hair.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyltrimethylammonium methyl sulfate, available from FeiXiang; hydrogenated tallow alkyl trimethyl ammonium chloride; stearyl dimethyl benzyl ammonium chloride; and stearoyl amidopropyl dimethyl benzyl ammonium chloride.

In an embodiment, the cationic surfactant can be chosen from those having a shorter alkyl group, i.e., $C_{16}$ alkyl group. Such cationic surfactants include, for example, cetyl trimethyl ammonim chloride. It is believed that cationic surfactants having a shorter alkyl group are advantageous for concentrated hair care oil nanoemulsion compositions described herein because they can improve shelf stability.

G. Water Miscible Solvents

The concentrated hair care compositions described herein may comprise from about 0.01% to about 25%, alternatively from about 0.01% to about 20%, and alternatively from about 0.01% to about 15% of a water miscible solvent, by weight of the concentrated hair care composition. In an embodiment, the concentrated hair care compositions described herein may comprise 0% of a water miscible solvent, by weight of the concentrated hair care composition. Non-limiting examples of suitable water miscible solvents include polyols, copolyols, polycarboxylic acids, polyesters and alcohols.

Examples of useful polyols include, but are not limited to, glycerin, diglycerin, propylene glycol, dipropylene glycol, ethylene glycol, butylene glycol, pentylene glycol, 1,3-butylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Examples of suitable alcohols include, but are not limited to ethanol, n-propanol, isopropanol, n-butanol, sec-butanol, tert-butanol, n-hexanol and cyclohexanol.

Other suitable water miscible solvents include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

In an embodiment, the water miscible solvents may be selected from the group consisting of glycerin, propylene glycol, dipropylene glycol, and mixtures thereof. EP 0283165 B1 discloses other suitable water miscible solvents, including glycerol derivatives such as propoxylated glycerol.

H. Viscosity Modifiers

The concentrated hair care composition described herein may comprise from about 0.001% to about 2%, alternatively from about 0.001% to about 1%, and alternatively from about 0.001% to about 0.5% of a viscosity modifier, by weight of the concentrated hair care composition. In an embodiment, the concentrated hair care composition described herein may comprise 0% of a viscosity modifier, by weight of the concentrated hair care composition. Non-limiting examples of suitable viscosity modifiers include water soluble polymers, cationic water soluble polymers, Examples of water soluble polymers include, but are not limited to (1) vegetable based polymers such as gum Arabic, tragacanth gum, galactan, guar gum, carob gum, karaya gum, carrageenan, pectin, agar, quince seed, algal colloid, starch (rice, corn, potato, or wheat), and glycyrrhizinic acid; (2) microorganism-based polymers such as xanthan gum, dextran, succinoglucan, and pullulan; and (3) animal-based polymers such as collagen, casein, albumin, and gelatin. Examples of semi-synthetic water-soluble polymers include (1) starch-based polymers such as carboxymethyl starch and methylhydroxypropyl starch; (2) cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, and cellulose powder; and (3) alginate-based polymers such as sodium alginate and propylene glycol alginate. Examples of synthetic water-soluble polymers include (1) vinyl-based polymers such as polyvinyl alcohol, polyvinyl methyl ether-based polymer, polyvinylpyrrolidone, and carboxyvinyl polymer (CARBOPOL 940, CARBOPOL 941; (2) polyoxyethylene-based polymers such as polyethylene glycol 20,000, polyethylene glycol 6,000, and polyethylene glycol 4,000; (3) copolymer-based polymers such as a copolymer of polyoxyethylene and polyoxypropylene, and PEG/PPG methyl ether; (4) acryl-based polymers such as poly(sodium acrylate), poly(ethyl acrylate), polyacrylamide, polyethylene imines, and cationic polymers. The water-swellable clay minerals are nonionic water-soluble polymers and correspond to one type of colloid-containing aluminum silicate having a triple layer structure. More particular, as examples thereof, mention may be made of bentonite, montmorillonite, beidellite, nontronite, saponite, hectorite, aluminum magnesium silicate, and silicic anhydride.

Examples of cationic water soluble polymers include, but are not limited to (1) quaternary nitrogen-modified polysaccharides such as cation-modified cellulose, cation-modified hydroxyethylcellulose, cation-modified guar gum, cation-modified locust bean gum, and cation-modified starch; (2) dimethyldiallylammonium chloride derivatives such as a copolymer of dimethyldiallylammonium chloride and acrylamide, and poly(dimethylmethylene piperidinium chloride); (3) vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, and a copolymer of vinylpyrrolidone and methylvinylimidazolium chloride; and (4) methacrylic acid derivatives such as a copolymer of methacryloylethyldimethylbetaine, methacryloylethyl trimethylammonium chloride and 2-hydroxyethyl methacrylate, a copolymer of methacryloylethyldimethylbetaine, and methacryloylethyl trimethylammonium chloride and methoxy polyethylene glycol methacrylate.

I. Viscosity

The concentrated hair care composition described herein may have a liquid phase viscosity of from about 1 centipoise to about 80 centipoise, alternatively from about 3 to about 60 centipoise, alternatively from about 5 to about 45 centipoise, and alternatively from about 10 to about 40 centipoise. In one embodiment, the concentrated hair care composition described herein may have a liquid phase viscosity of from about 1 centipoise to about 150 centipoise, alternatively from about 2 centipoise to about 100 centipoise, alternatively from about 3 centipoise to about 60 centipoise, alternatively from about 5 centipoise to about 45 centipoise, and alternatively from about 10 centipoise to about 40 centipoise.

The viscosity values may be measured employing any suitable rheometer or viscometer at 25.0° C. and at a shear rate of about 2 reciprocal seconds. The viscosity values reported herein were measured using a TA Instruments AR-G2 Rheometer with a concentric cylinder attachment (cup with a diameter of 30.41 mm; a bob with a diameter of 27.98 mm and a length of 42.02 mm; and a concentric cyclinder jacket assembly) at a shear rate of 2 reciprocal seconds at 25° C.

J. Optional Ingredients

The concentrated hair care composition described herein may optionally comprise one or more additional components known for use in hair care or personal care products, provided that the additional components are physically and chemically compatible with the essential components described herein, or do not otherwise unduly impair product stability, aesthetics or performance Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the conditioning composition.

Additional emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, cationic polymers, viscosity modifiers, coloring agents or dyes, conditioning agents, hair bleaching agents, thickeners, moisturizers, foam boosters, additional surfactants or nonionic cosurfactants, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, non-volatile solvents or diluents (water-soluble and water-insoluble), co-solvents or other additional solvents, and similar other materials.

K. Mechanical Foam Dispenser

The mechanical foam dispenser described herein may be selected from the group consisting of squeeze foam dispensers, pump foam dispensers, other mechanical foam dispensers, and combinations thereof. In an embodiment, the mechanical foam dispenser is a squeeze foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The mechanical foam dispenser may comprise a reservoir for holding the concentrated hair treatment composition. The reservoir may be made out of any suitable material selected from the group consisting of plastic, metal, alloy, laminate, and combinations thereof. The reservoir may be a refillable reservoir such as a pour-in or screw-on reservoir, or the reservoir may be for one-time use. The reservoir may also be removable from the mechanical foam dispenser. Alternatively, the reservoir may be integrated with the mechanical foam dispenser. In an embodiment, there may be two or more reservoirs.

In an embodiment, the reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

The concentrated hair care composition may be dispensed as a foam wherein the foam has a density of from about 0.025 g/cm³ to about 0.30 g/cm³, alternatively from about 0.035 g/cm³ to about 0.25 g/cm³, alternatively from about 0.05 g/cm³ to about 0.20 g/cm³, and alternatively from about 0.055 g/cm³ to about 0.15 g/cm³.

The concentrated hair care composition can be dispensed at a dosage weight of from about 1 g to about 8 g, alternatively from about 1 g to about 7 g, alternatively from about 1 g to about 6 g, and alternatively from about 1 g to about 5 g. The dosage may be achieved by any manner of mechanical foaming as described above in either discrete or continuous foaming incidents. In the case of pump or squeeze foamers, the dosage may be achieved at from about 1 to about 10 pumps or squeezes, alternatively at from about 1 to about 7 pumps or squeezes, alternatively at from about 1 to about 5 pumps or squeezes, and alternatively at about 1 to about 3 pumps or squeezes. A continuous mechanical foamer may also include connection to a separate power source such as a battery or electrical outlet.

L. Water

The concentrated hair care composition described herein may comprise from about from about 60% to about 90% water, alternatively from about 65% to about 87.5%, alternatively from about 67.5% to about 85%, alternatively from about 70% to about 82.5%, and alternatively from about 72.5% to about 80% water, by weight of the concentrated hair care composition.

Method of Treating Hair

The method of treating the hair described herein comprises (1) providing a concentrated hair care composition, as described herein, in a mechanical foam dispenser, (2) dispensing the concentrated hair care composition from the mechanical foam dispenser as a dosage of foam; (3) applying the foam to the hair; and (4) rinsing the foam from the hair.

Examples

The following examples illustrate the concentrated hair care composition described herein. The exemplified compositions can be prepared by conventional formulation and mixing techniques. It will be appreciated that other modifications of the concentrated hair care composition described herein within the skill of those in the art can be undertaken without departing from the spirit and scope of the composition described herein. All parts, percentages, and ratios herein are by weight unless otherwise specified. Some components may come from suppliers as dilute solutions. The amount stated reflects the weight percent of the active material, unless otherwise specified.

The following area non-limiting examples of the composition described herein.

Non-Silicone Concentrated Nanoemulsion Premixes

The following soybean oil nanoemulsion premixes were made by the phase inversion temperature method:

| Raw Material | Ex. PE 1 | Ex. PE 2 |
|---|---|---|
| Soybean Oil | 10.0% | 10.0% |
| Polyoxyethylene (10) oleyl ether[1] | 7.5% | 20.0% |
| Water | Q.S. | Q.S. |
| Emulsification Process | Phase Inversion | Phase Inversion |
| Surfactant Level | 7.5% | 20% |
| Oil Level | 5% | 10 |
| HLB | 12 | 12 |
| Particle Size | 33 nm | 27 nm |

[1]Brij™ O10 (97% active) available from Croda, Inc.

1 Brij™ O10 (97% active) available from Croda, Inc.

The nanoemulsion premixes were made by:

1. Adding all of the raw materials to a glass beaker;
2. Heating the mixture (in a hot water bath) up to 94 degrees Celsius while stirring (covered under foil to minimize evaporation);
3. Turning the heat off;
4. Replacing the hot water with cold tap water;
5. Once the temperature reaches below 60 degrees Celsius, ice is added to the cold water bath; and
6. Continuing to sir the composition during the remaining cool down to room temperature.

Non-Silicone Concentrated Nanoemulsion Foam Conditioners

| Raw Material | Ex. 1 | Ex. 1 | Ex. 1 | Ex. 1 | Ex 2 |
|---|---|---|---|---|---|
| Soybean oil nanoemulsion (Ex. PE 2)[1] | 89% | 70% | 60% | 50% | 40% |
| Cetyl alcohol | 0% | 0% | 0% | 0% | 0% |
| Stearyl alcohol | 0% | 0% | 0% | 0% | 0% |
| Behenyltrimethylammonium methosulfate | 0% | 0% | 0% | 0% | 0% |
| Cetyltrimethylammonium chloride | 2.50% | 2.50% | 2.50% | 2.50% | 2.50% |
| Ethylenediaminetetraacetic acid, disodium salt | 0.13% | 0.13% | 0.13% | 0.13% | 0.13% |
| Benzyl alcohol | 0.4% | 0.4% | 0.4% | 0.4% | 0.4% |
| 5-chloro-2-methyl-4-isothiazolin-3-one and 2-methyl-4-isothiazolin-3-one[2] | 0.03% | 0.03% | 0.03% | 0.03% | 0.03% |
| Citric Acid | 0.02% | 0.02% | 0.02% | 0.02% | 0.02% |
| Perfume | 2.00% | 2.00% | 2.00% | 2.00% | 2.00% |
| Water | q.s. | q.s. | q.s. | q.s. | q.s. |
| Weight % of oil | 8.9% | 7.0% | 6.0% | 5.0% | 4.0% |
| Weight % of high melting point fatty compounds | 0% | 0% | 0% | 0% | 0% |
| Weight ratio of oil to high melting point fatty compounds | Infinity | Infinity | Infinity | Infinity | Infinity |

[1]Nanoemulsion from Example PE 2 comprising 10% active soybean oil
[2]Kathon™ CG available from Dow Chemical Company.

The above non-silicone concentrated nanoemulsion foam conditioners of the concentrated hair care composition described herein were prepared by weighing distilled water, the soybean oil nanoemulsion from example PE2 and disodium EDTA in a beaker. The beaker is placed in a water bath on a hot plate while mixing with overhead mixer at 100 to 150 rpm. Cetyltrimethylammonium choloride is then added. When the materials are all heated thoroughly towards a uniform product, the heating is stopped while the mixture is continued to stir. The batch is cooled to 35 C by removing the hot water from the water bath and replacing with cold water. The perfume and Kathon are added and with continued stirring for ~10 minutes. The resulting ultra-low viscosity conditioner formulas can be delivered and dispensed by known mechanical foam dispensers (pump or squeeze foamers etc.).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating the hair, the method comprising:
    a) providing a concentrated hair conditioner composition in a mechanical foam dispenser, wherein the concentrated hair conditioner composition comprises:
        i) from about 4% to about 15% of soybean oil, by weight of the concentrated hair conditioner composition, wherein the particle size of the soybean is from about 12 nm to about 50 nm;
        ii) 0% fatty alcohol selected from the group consisting of cetyl alcohol, stearyl alcohol, behenyl alcohol, and mixtures thereof;
        iii) from about 1% to about 5% perfume, by weight of the concentrated hair conditioner composition;
        iv) from about 5% to about 20% of a nonionic emulsifier wherein the nonionic emulsifier is polyoxyethylene (10) oleyl ether; and
        v) from about 60% to about 90% water, by weight of the concentrated hair conditioner composition;
        vi) from about 0.5% to about 4% cetyl trimethyl ammonium chloride;
        wherein the concentrated hair conditioner composition has a liquid phase viscosity of from about 1 centipoise to about 80 centipoise;
        wherein the hair conditioner composition is silicone-free;
    b) dispensing the concentrated hair conditioner composition from the mechanical foam dispenser as a dosage of foam;
    c) applying the foam to the hair; and
    d) rinsing the foam from the hair;
        wherein the foam has a density of from about 0.025 g/cm$^3$ to about 0.3 g/cm$^3$ when dispensed from the mechanical foam dispenser.

2. The method of claim 1, wherein the foam comprises a oil deposition purity of from about 90% to about 100% after applying the foam to the hair and rinsing the foam from the hair.

3. The method of claim 1 comprising from about 5% to about 15% of a nonionic emulsifier.

4. The method of claim 1, wherein the concentrated hair conditioner composition comprises from about 8% to about 18% of the soybean oil, by weight of the concentrated hair conditioner composition.

5. The method of claim 1, wherein the concentrated hair conditioner composition comprises from about 1.5% to about 4.5% perfume, by weight of the concentrated hair conditioner composition.

6. The method of claim 1, wherein the foam has a dosage weight of from about 1 g to about 5 g when dispensed from the mechanical foam dispenser.

7. The method of claim 1, wherein the density of the foam is from about 0.035 g/cm$^3$ to about 0.25 g/cm$^3$.

8. The method of claim 1, wherein the viscosity is from about 5 centipoise to about 45 centipoise.

9. The method of claim 1, wherein the viscosity is from about 10 centipoise to about 40 centipoise.

* * * * *